(12) United States Patent
Kaiwa et al.

(10) Patent No.: US 12,364,872 B2
(45) Date of Patent: Jul. 22, 2025

(54) VIVO-IMPLANTABLE MEDICAL DEVICE

(71) Applicant: Murata Manufacturing Co., Ltd., Kyoto-fu (JP)

(72) Inventors: Koyo Kaiwa, Nagaokakyo (JP); Takahiro Nagai, Nagaokakyo (JP); Tatsuya Hosotani, Nagaokakyo (JP)

(73) Assignee: Murata Manufacturing Co., Ltd., Kyoto-fu (JP)

( * ) Notice: Subject to any disclaimer, the term of this patent is extended or adjusted under 35 U.S.C. 154(b) by 600 days.

(21) Appl. No.: 17/814,286

(22) Filed: Jul. 22, 2022

(65) Prior Publication Data
US 2022/0362561 A1    Nov. 17, 2022

Related U.S. Application Data

(63) Continuation of application No. PCT/JP2020/031478, filed on Aug. 20, 2020.

(30) Foreign Application Priority Data

Jan. 23, 2020   (JP) .................................. 2020-009290

(51) Int. Cl.
*H02J 7/00*      (2006.01)
*A61N 1/378*     (2006.01)
*H02J 50/12*     (2016.01)

(52) U.S. Cl.
CPC ............ *A61N 1/3787* (2013.01); *H02J 50/12* (2016.02)

(58) Field of Classification Search
USPC ................... 320/106, 107, 108, 109, 110
See application file for complete search history.

(56) References Cited

U.S. PATENT DOCUMENTS

2009/0171420 A1   7/2009 Brown et al.
2012/0059238 A1*  3/2012 Wolf ................. A61B 5/031
                                                  600/377

FOREIGN PATENT DOCUMENTS

JP           5041610 B2    10/2012
JP         2017-164192 A    9/2017
(Continued)

OTHER PUBLICATIONS

International Search Report issued in PCT/JP2020/031478; mailed Nov. 10, 2020.

*Primary Examiner* — Brian Ngo
(74) *Attorney, Agent, or Firm* — Studebaker Brackett PLLC

(57) ABSTRACT

An in vivo-implantable medical device includes a housing that includes a body part and a protruding part, and that forms a sealed inner space; a power-receiving coil in a part of the inner space and that receives power by interlinking with external magnetic flux generated by an AC current flowing in an externally located power-transmitting coil; and a circuit substrate including a power reception circuit electrically connected to the power-receiving coil. The body part includes a metallic biocompatible material and the protruding part includes a non-metallic biocompatible material. The protruding part is structured so that, for a magnetic path along which the external magnetic flux passes, a magnetic path in which the magnetic flux interlinks with the power-receiving coil while avoiding the body part is formed, and the protruding part reduces eddy current loss caused by eddy currents generated by the external magnetic flux interlinking with the body part.

20 Claims, 5 Drawing Sheets

(56) References Cited

FOREIGN PATENT DOCUMENTS

| JP | 2018-501021 A | 1/2018 | | |
|---|---|---|---|---|
| WO | 2016/190095 A1 | 12/2016 | | |
| WO | WO-2020066095 A1 | * | 4/2020 | ........... A61B 5/0026 |

* cited by examiner

VIVO-IMPLANTABLE MEDICAL DEVICE

CROSS-REFERENCE TO RELATED APPLICATIONS

This application claims benefit of priority to International Patent Application No. PCT/JP2020/031478, filed Aug. 20, 2020, and to Japanese Patent Application No. 2020-009290, filed Jan. 23, 2020, the entire contents of each are incorporated herein by reference.

BACKGROUND

Technical Field

The present disclosure relates to an in vivo-implantable medical device that is used by being implanted (embedded) inside a living body such as the body of a person or an animal and is powered by being wirelessly supplied with power from outside the body.

Background Art

Heretofore, various technologies that can be applied to in vivo-implantable medical devices have been proposed.

Japanese Unexamined Patent Application Publication No. 2017-164192 discloses an in vivo-implantable medical device used as a pacemaker. This in vivo-implantable medical device includes a housing, a power-receiving coil, a secondary battery, and a driving device. The housing houses the power-receiving coil, the secondary battery, and the driving device. The power-receiving coil receives power from outside the body through electromagnetic induction by interlinking with magnetic flux. The secondary battery stores power received by the power-receiving coil. The driving device drives the secondary battery as a power source. The driving device includes a control circuit that performs pacing on the basis of electrocardiographic data, for example.

Furthermore, Japanese Patent No. 5041610 discloses a wireless charging device used with a pacemaker or the like.

SUMMARY

In the in vivo-implantable medical device disclosed in Japanese Unexamined Patent Application Publication No. 2017-164192, the housing that houses the power-receiving coil is composed of metal. Therefore, eddy currents are generated in the housing by the magnetic flux generated in order to perform wireless power supply and the housing heats up due to eddy current loss. Consequently, there is a concern that the living body in which the in vivo-implantable medical device has been implanted will be adversely affected. Furthermore, it is not easy to increase the magnetic coupling between the power-receiving coil and the power-transmitting coil and this makes it difficult to improve power efficiency in power reception. In the wireless charging device disclosed in Japanese Patent No. 5041610 as well, since the housing is composed of metal, the same problems arise.

On the other hand, if the housing of an in vivo-implantable medical device is made of a non-metallic material, no eddy currents will be generated in the housing during wireless power supply and heating up of the housing due to eddy current loss can be suppressed. In addition, the magnetic coupling between the power-receiving coil and the power-transmitting coil will not be disturbed. However, typical known non-metallic materials having good biocompatibility such as sapphire, ruby, glass, or ceramic are not easy to process and it is difficult to form a housing from these materials.

Accordingly, the present disclosure provide an in vivo-implantable medical device that can reduce heating up of a housing resulting from eddy current loss caused by generation of eddy currents in the housing by magnetic flux generated for wireless power supply and that has high power efficiency in power reception.

An in vivo-implantable medical device of the present disclosure includes a housing that includes a body part having an opening and a protruding part provided so as to close the opening, such that the housing forms a sealed inner space; a power-receiving coil that is disposed in a part of the inner space formed by the protruding part and that receives power by interlinking with external magnetic flux generated by an AC current flowing in an externally located power-transmitting coil; and a circuit substrate that is provided with a power reception circuit electrically connected to the power-receiving coil and that is disposed in the inner space so as to be further from a protruding end of the protruding part than the power-receiving coil. The body part is formed of a metallic biocompatible material and the protruding part is formed of a non-metallic biocompatible material. The protruding part is structured so that, for a magnetic path along which the external magnetic flux passes, a magnetic path in which magnetic flux interlinks with the power-receiving coil while avoiding the body part is formed. The protruding part is provided so as to reduce eddy current loss caused by eddy currents generated by the external magnetic flux interlinking with the body part.

The present disclosure provides an in vivo-implantable medical device that can reduce heating up of a housing resulting from eddy current loss caused by generation of eddy currents in the housing by magnetic flux generated for wireless power supply and that has high power efficiency in power reception.

DETAILED DESCRIPTION

Hereafter, a plurality of modes for carrying out the present disclosure will be described. Each embodiment is an illustrative example and parts of the configurations described in different embodiments can be substituted for one another or combined with one another. In each embodiment, points that are different from those described prior to that embodiment are described. In particular, the same operational effects resulting from the same configurations are not repeatedly described in the individual embodiments.

First Embodiment

Figure 1:
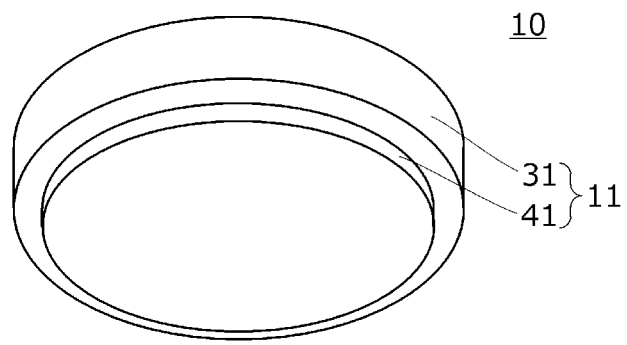
FIG. 1 is an external perspective view of an in vivo-implantable medical device according to a First Embodiment of the present disclosure.
Figure 2:
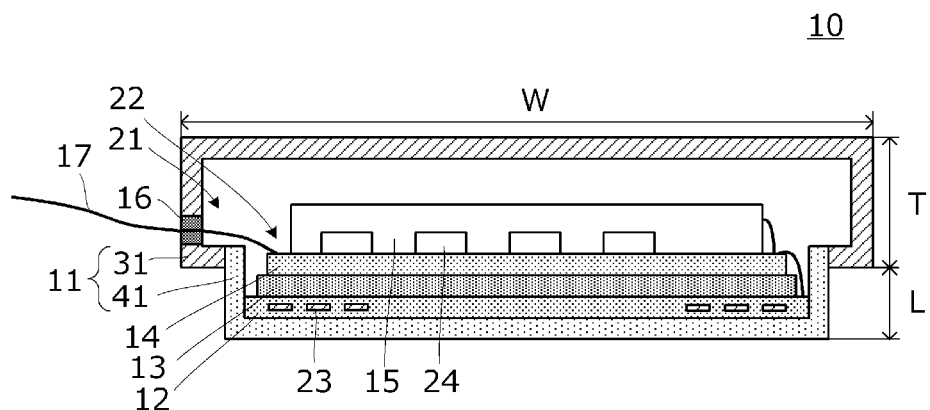
FIG. 2 is a sectional view of the in vivo-implantable medical device.
Figure 3:
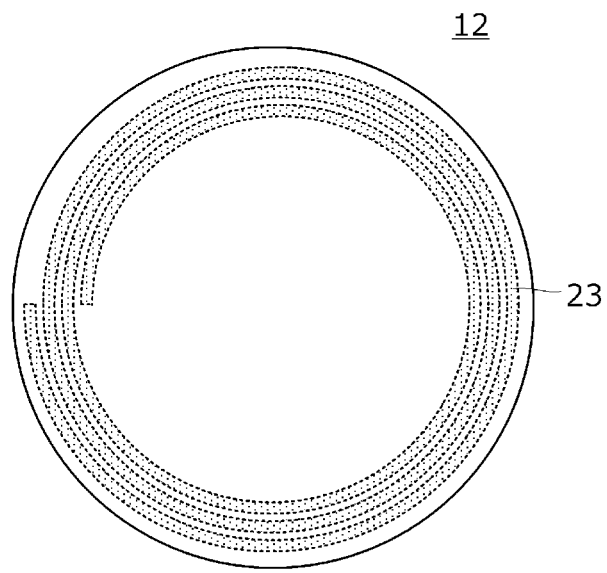
FIG. 3 is a plan view of a coil substrate.
Figure 4:
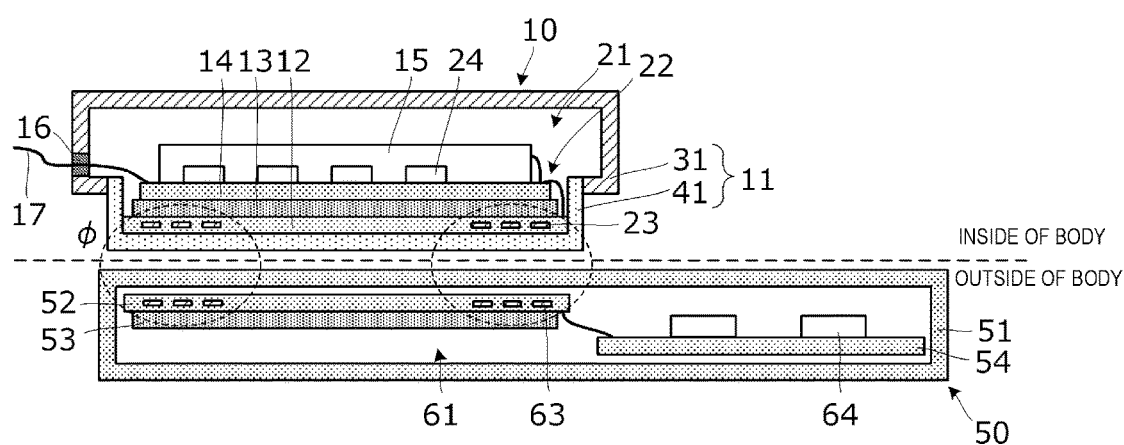
FIG. 4 is a sectional view of a power supply system according to the First Embodiment of the present disclosure.
Figure 5:
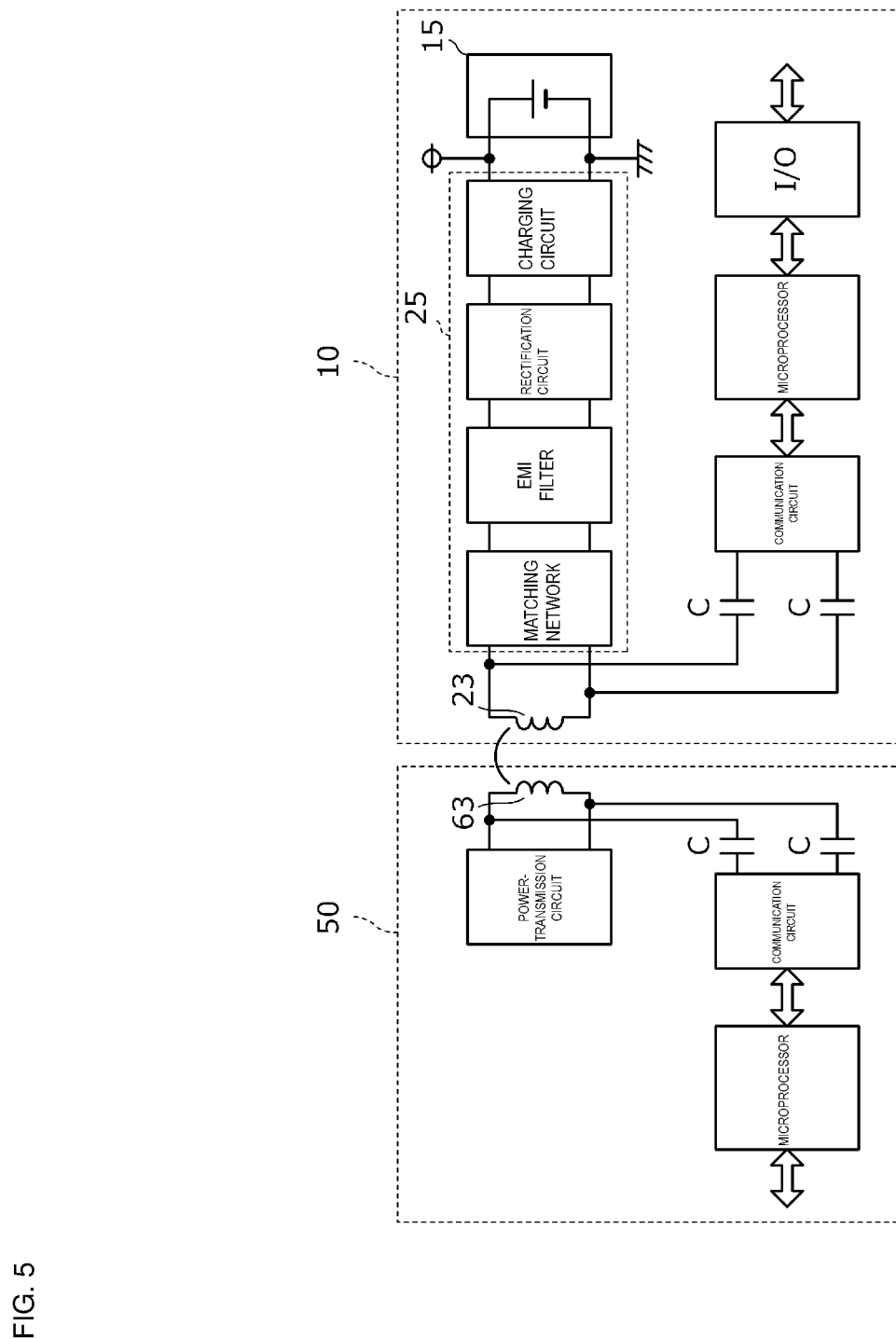
FIG. 5 is a block diagram illustrating the circuit configuration of the power supply system according to the First Embodiment of the present disclosure.

FIG. 1 is an external perspective view of an in vivo-implantable medical device 10 according to a First Embodiment of the present disclosure. FIG. 2 is a sectional view of the in vivo-implantable medical device 10. FIG. 3 is a plan view of a coil substrate 12. In FIG. 3, illustration of wiring led out from the two ends of a power-receiving coil 23 is omitted. FIG. 4 is a sectional view of a power supply system according to the First Embodiment of the present disclosure. FIG. 5 is a block diagram illustrating the circuit configuration of the power supply system according to the First Embodiment of the present disclosure.

As illustrated in FIGS. 1 and 2, the in vivo-implantable medical device 10 includes a housing 11, a coil substrate 12, a magnetic sheet 13, a circuit substrate 14, a power storage device 15, a feed through 16, and a biosensor 17. The housing 11 includes a body part 31 and a protruding part 41. The coil substrate 12 is provided with the power-receiving coil 23.

The body part 31 has an opening 22. The protruding part 41 is provided so as to close the opening 22. The housing 11 forms a sealed inner space 21. The power-receiving coil 23 is disposed in a part of the inner space 21 formed by the protruding part 41. The power-receiving coil 23 receives power by interlinking with external magnetic flux φ generated by an AC current flowing through a power-transmitting coil 63 (refer to FIG. 4), which is located outside the housing 11. The circuit substrate 14 is provided with a power reception circuit 25 (refer to FIG. 5) that is electrically connected to the power-receiving coil 23. The circuit substrate 14 is disposed in the inner space 21 so as to be further from a protruding end of the protruding part 41 than the power-receiving coil 23. The body part 31 is formed of a metallic biocompatible material. The protruding part 41 is formed of a non-magnetic non-metallic biocompatible material. The protruding part 41 is structured so that, for a magnetic path along which the external magnetic flux φ passes, a magnetic path in which the magnetic flux interlinks with the power-receiving coil 23 while avoiding the body part 31 is formed and the protruding part 41 is provided so as to reduce eddy current loss caused by eddy currents generated by the external magnetic flux φ interlinking with the body part 31.

The body part 31 consists of a top plate portion, a bottom plate portion, and a side wall portion. The opening 22 is formed in the bottom plate portion of the body part 31. The protruding part 41 is provided so as to protrude from the bottom plate portion of the body part 31. The protruding part 41 consists of the bottom plate portion and the side wall portion. The bottom plate portion of the protruding part 41 corresponds to the protruding end of the protruding part 41 mentioned above. The body part 31 and the protruding part 41 are bonded to each other using a biocompatible adhesive, for example.

A thickness T of the body part 31 is larger than a length L by which the protruding part 41 protrudes and is smaller than a width W of the body part 31 (diameter of top plate portion of body part 31). In other words, a dimension of the body part 31 in the protruding direction of the protruding part 41 is larger than the length by which the protruding part 41 protrudes and is smaller than a dimension of the body part 31 in an arbitrary direction perpendicular to the protruding direction of the protruding part 41. The width W of the body part 31 is around 30 mm, for example.

Note that although the body part 31 and the protruding part 41 have a circular shape in plan view (looking in the protruding direction of the protruding part 41), the body part 31 and the protruding part 41 may instead have a rectangular shape or another shape in plan view.

The metallic biocompatible material forming the body part 31 is preferably a material mainly composed of titanium or a titanium alloy. For example, the body part 31 is composed of pure titanium or a titanium alloy such as Ti-6Al-4V. Alternatively, the body part 31 is composed of a sintered mixed material consisting of a ceramic powder and a powder of the titanium alloy. By using such a metallic biocompatible material for the body part 31, the effect of the material on a living body and the effect on the material from the living body can be suppressed. Furthermore, the weight of the body part 31 can be reduced and the durability of the body part 31 can be improved by using a titanium material for the body part 31.

Although titanium or a titanium alloy is preferably used as the main component of the metallic biocompatible material as described above, a material such as stainless steel containing chromium or molybdenum, Co—Cr alloys, and so on can also be used as a metallic biocompatible material. A material that provides durability to the environment, stress, and so on is preferably used as the metallic biocompatible material, and for example, a material having a Young's modulus of 100 GPa or higher is more preferable.

The non-metallic biocompatible material forming the protruding part 41 is preferably sapphire, ruby, glass, or a ceramic. By using such as non-metallic biocompatible material for the protruding part 41, the effect of the material on a living body and the effect on the material from the living body can be suppressed.

It is preferable that a fine ceramic as represented by the chemical formula $Al_2O_3$ be used as the above-mentioned ceramic from the viewpoint of environmental durability. Glass is preferred as the non-metallic biocompatible material when ease of processing is important. Furthermore, tempered glass, which is excellent in terms of durability, may be used as the non-metallic biocompatible material.

The protruding part 41 is formed by cutting and digging into a plate-shaped non-metallic biocompatible material, for example.

Figure 6:
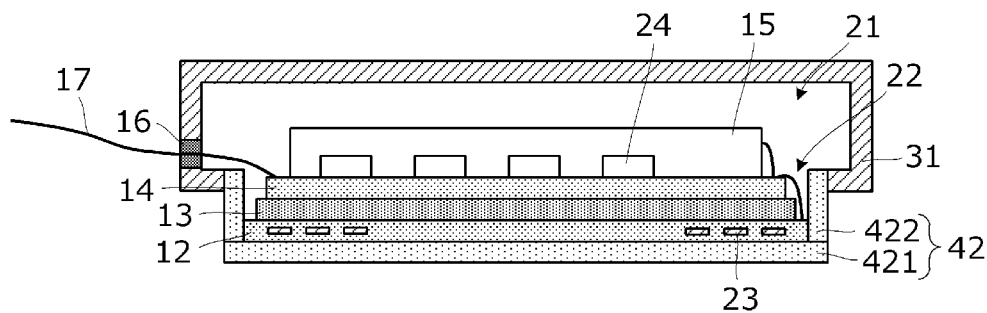
FIG. 6 is a sectional view of an in vivo-implantable medical device according to a modification of the First Embodiment of the present disclosure.

As illustrated in FIG. 6, a protruding part 42 may be provided instead of the protruding part 41. The protruding part 42 consists of a bottom plate portion 421 and a side wall portion 422 that are bonded to each other using a biocompatible adhesive.

The coil substrate 12, the magnetic sheet 13, and the circuit substrate 14 are stacked in this order on the bottom plate portion of the protruding part 41.

The coil substrate 12 is disposed so as to contact the bottom plate portion of the protruding part 41. In other words, the coil substrate 12 is disposed outside the body part 31. The coil substrate 12 consists of an insulating substrate and the power-receiving coil 23. The power-receiving coil 23 receives power by interlinking with magnetic flux from outside the living body. As illustrated in FIG. 3, the power-receiving coil 23 is, for example, formed of a conductor pattern having a helical (spiral) shape in a single layer inside the insulating substrate. The winding axis direction of the power-receiving coil 23 substantially coincides with the protruding direction of the protruding part 41. The power-receiving coil 23 is electrically connected to a conductor pattern (not illustrated) of the circuit substrate 14, which is described later.

Note that the outer shapes of the coil substrate 12 and the power-receiving coil 23 are circular in plan view, but may instead be rectangular or other shapes. Furthermore, the power-receiving coil 23 may be formed on a main surface of the insulating substrate or may be formed across a plurality of layers of the insulating substrate.

The magnetic sheet 13 is disposed between the power-receiving coil 23 and the circuit substrate 14. The magnetic sheet 13 is disposed in a part of the inner space 21 formed by the protruding part 41. In other words, the magnetic sheet 13 is disposed outside the body part 31. With the magnetic sheet 13, a magnetic path is formed in which magnetic flux interlinks with the power-receiving coil 23 while also avoiding the body part 31. The magnetic sheet 13 is smaller than the opening 22 of the body part 31 and larger than the outer shape of the power-receiving coil 23 and the circuit substrate 14 in plan view. The magnetic flux $\varphi$ can be prevented from affecting the circuit substrate 14 and the power storage device 15 by disposing the magnetic sheet 13, which is larger than the outer shape of the power-receiving coil 23, between the power-receiving coil 23 and the circuit substrate 14.

The magnetic sheet 13 may be disposed inside the body part 31 and may be larger than the opening 22 in plan view. In addition, the magnetic sheet 13 preferably does not contact the body part 31, but may contact the body part 31 to some extent.

The circuit substrate 14 includes an insulating substrate on and/or in which a conductor pattern is formed and a plurality of electronic components 24 mounted on the insulating substrate. The electronic components 24 include, for example, a biosensor, an IC, and a passive element. The conductor pattern and electronic components 24 of the circuit substrate 14 form circuits of a power supply system, a signal processing system, and an arithmetic system described below.

The power storage device 15 is provided on the circuit substrate 14 and is electrically connected to the conductor pattern of the circuit substrate 14. The power storage device 15 is, for example, a thin secondary battery. The power storage device 15 stores power received by the power-receiving coil 23.

The feed through 16 is provided in the side wall portion or top plate portion of the body part 31. The biosensor 17 is led out via the feed through 16 to outside the housing 11. The biosensor 17 is electrically connected to the conductor pattern of the circuit substrate 14 inside the housing 11 via the feed through 16.

As illustrated in FIG. 4, the power supply system according to the First Embodiment includes the in vivo-implantable medical device 10 and a power-transmitting device 50. The in vivo-implantable medical device 10 is disposed inside a living body and the power-transmitting device 50 is disposed outside the living body. The in vivo-implantable medical device 10 is disposed so that the protruding direction of the protruding part 41 faces outward from the living body.

The power-transmitting device 50 includes a housing 51, a coil substrate 52, a magnetic sheet 53, and a circuit substrate 54. The housing 51 is formed of a non-metallic material such as a resin. The coil substrate 52, the magnetic sheet 53, and the circuit substrate 54 are disposed in an inner space 61 of the housing 51. The coil substrate 52 includes an insulating substrate and the power-transmitting coil 63. The circuit substrate 54 includes an insulating substrate on and/or in which a conductor pattern (not illustrated) is formed and a plurality of electronic components 64 mounted on the insulating substrate. The power-transmitting coil 63 is, for example, formed of a conductor pattern having a spiral shape in a single layer inside the insulating substrate. The power-transmitting coil 63 is electrically connected to the conductor pattern of the circuit substrate 54. The electronic components 64 include, for example, a power supply IC and a passive component. The conductor pattern and the electronic components 64 of the circuit substrate 54 form the circuit of the power-transmitting device 50, which is described later. The magnetic sheet 53 is provided so as to contact a main surface of the coil substrate 52.

The power-transmitting device 50 is disposed close to the in vivo-implantable medical device 10 so that the power-transmitting coil 63 is in a prescribed positional relationship with the power-receiving coil 23. At this time, the power-transmitting device 50 is disposed so that the power-transmitting coil 63 is interposed between the magnetic sheet 13 and the magnetic sheet 53. In this arrangement state, the power-transmitting coil 63 and the power-receiving coil 23 magnetically couple with each other and power is supplied from the power-transmitting device 50 to the in vivo-implantable medical device 10. This power is stored in the power storage device 15 and is supplied to the electronic components 24 and so forth.

The power-transmitting coil 63 and the power-receiving coil 23 are disposed so as to be interposed between the magnetic sheet 13 and the magnetic sheet 53 during power supply. This strengthens the magnetic coupling between the power-transmitting coil 63 and the power-receiving coil 23 and therefore power efficiency in power reception is improved.

As illustrated in FIG. 5, the power-transmitting device 50 is provided with the power-transmitting coil 63, a power transmission circuit electrically connected to the power-transmitting coil 63, a communication circuit, a microprocessor, and so on. The in vivo-implantable medical device 10 is provided with the power-receiving coil 23, the power reception circuit 25, and the power storage device 15. The power reception circuit 25 includes a matching network, an EMI filter, a rectification circuit, and a charging circuit. A power supply circuit is formed by these circuits. Furthermore, the in vivo-implantable medical device 10 is provided with a communication circuit, a microprocessor, and an I/O circuit. Signal processing and arithmetic circuits are formed by these circuits. The communication circuit is electrically connected to the power-receiving coil 23 via capacitors C.

The matching network realizes impedance matching. The EMI filter removes an electromagnetic noise component. The rectification circuit transforms AC power received by the power-receiving coil 23 into DC power. The charging circuit controls charging of the power storage device 15 with DC power output from the rectification circuit.

The I/O circuit inputs and outputs signals to and from various sensors electrically connected thereto. The microprocessor performs prescribed signal processing and arithmetic processing. The communication circuit outputs data to the power-transmitting device 50 or to other external devices such as measurement devices and medical devices. This data is outputted by superimposing a signal having a prescribed format on a current flowing in the power-receiving coil 23. The microprocessor and the communication circuit operate with the power storage device 15 serving as a power supply.

This circuit configuration enables the in vivo-implantable medical device 10 to receive power and perform communication wirelessly.

The microprocessor and prescribed circuits electrically connected to the I/O circuit may form, for example, a control circuit that performs pacing on the basis of electrocardiographic data, a signal processing circuit that processes signals obtained by sensing biological signals, and a biological signal generating circuit that provides electrical signals to muscles.

According to the First Embodiment, the power-receiving coil 23 is disposed in a part of the inner space 21 formed by the protruding part 41. Therefore, in wireless power supply, the power-transmitting coil 63 and the power-receiving coil 23, which are disposed close to each other, are disposed so as to be spaced apart from the body part 31. As a result, a magnetic path is formed, for the magnetic path along which the external magnetic flux $\varphi$ passes, in which the magnetic flux interlinks with the power-receiving coil 23 while avoiding the body part 31. The body part 31 is formed of a metallic biocompatible material and the protruding part 41 is formed of a non-metallic biocompatible material. Therefore, it is possible to reduce heating up of the housing 11 caused by eddy current loss resulting from eddy currents being generated in the housing 11 due to the external magnetic flux $\varphi$ interlinking with the housing 11.

Furthermore, the power-transmitting coil 63 and the power-receiving coil 23 face each other across a non-metallic biocompatible material rather than a metallic biocompatible material. Therefore, high power efficiency is obtained in power reception without disturbing the magnetic coupling between the power-transmitting coil 63 and the power-receiving coil 23.

Furthermore, according to the First Embodiment, an easily processed metallic biocompatible material is used for the main part of the housing 11 and a non-metallic biocompatible material is only used for part of the housing 11. Therefore, the housing 11 is not very difficult to manufacture.

Furthermore, the magnetic sheet 13 is disposed between the power-receiving coil 23 and the body part 31 and does not contact the body part 31. Therefore, it is more difficult for the external magnetic flux $\varphi$ to reach the body part 31 and interlinking of the external magnetic flux $\varphi$ with the body part 31 is further reduced.

In addition, the coil substrate 12 is disposed so as to not contact the body part 31. Therefore, heat generated by the power-receiving coil 23 during wireless power supply is less likely to be transferred to the body part 31 and an increase in the temperature of the body part 31 is suppressed.

Second Embodiment

Figure 7:
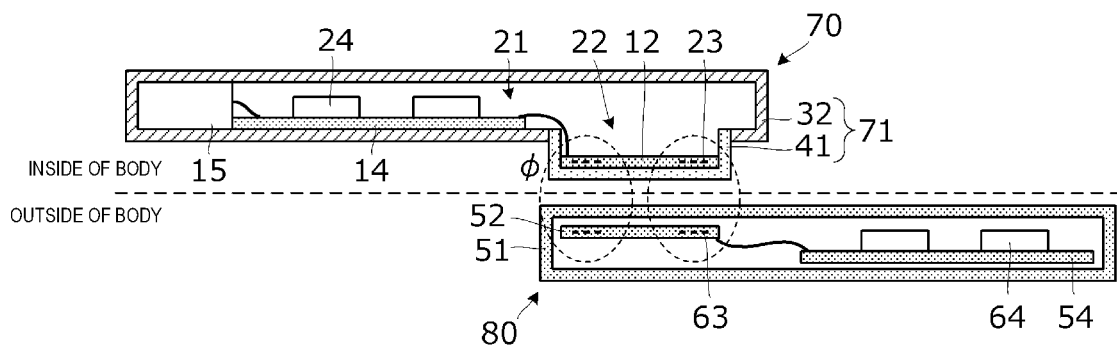
FIG. 7 is a sectional view of a power supply system according to a Second Embodiment of the present disclosure.

FIG. 7 is a sectional view of a power supply system according to a Second Embodiment of the present disclosure. This power supply system includes an in vivo-implantable medical device 70 and a power-transmitting device 80. The in vivo-implantable medical device 70 includes a housing 71, a coil substrate 12, a circuit substrate 14, and a power storage device 15. The housing 71 includes a body part 32 and a protruding part 41.

The body part 32 is formed in a thin box-like shape. The body part 32 consists of a top plate portion, a bottom plate portion, and a side wall portion. The bottom plate portion of the body part 32 has an opening 22 near an end portion thereof. The protruding part 41 is provided so as to close the opening 22. The coil substrate 12, the circuit substrate 14, and the power storage device 15 are provided in an inner space 21 of the housing 71. The coil substrate 12 is disposed on the bottom plate portion of the protruding part 41. The circuit substrate 14 and the power storage device 15 are disposed inside the body part 32. The coil substrate 12, the circuit substrate 14, the power storage device 15 are disposed next to each other along a width direction of the body part 32. The in vivo-implantable medical device 70 and the power-transmitting device 80 are not provided with magnetic sheets.

According to the Second Embodiment, the circuit substrate 14 and the power storage device 15 are disposed so as to be spaced apart from the power-receiving coil 23 in the width direction of the body part 32. Therefore, it is much less likely that the external magnetic flux $\varphi$ will reach the circuit substrate 14 and the power storage device 15. As a result, the external magnetic flux $\varphi$ does not affect the circuit substrate 14 and the power storage device 15 even though magnetic sheets are not provided.

Third Embodiment

Figure 8:
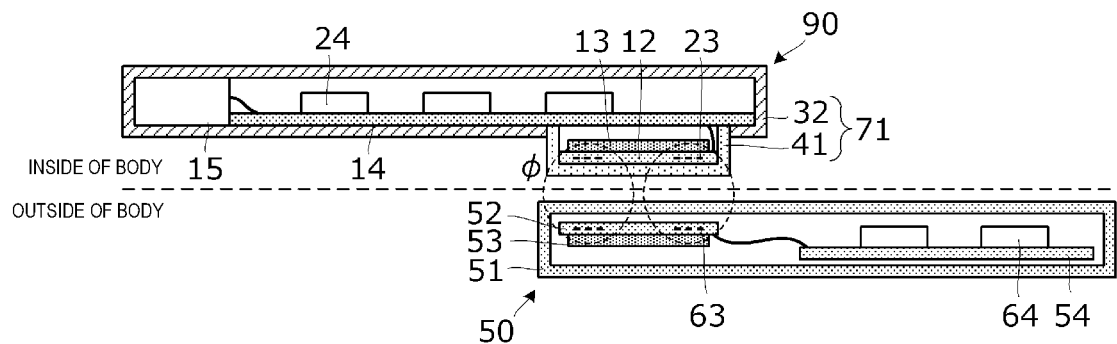
FIG. 8 is a sectional view of a power supply system according to a Third Embodiment of the present disclosure.

FIG. 8 is a sectional view of a power supply system according to a Third Embodiment of the present disclosure. This power supply system includes an in vivo-implantable medical device 90 and a power-transmitting device 50.

The in vivo-implantable medical device 90 differs from the in vivo-implantable medical device 70 according to the Second Embodiment in the following ways. Part of the circuit substrate 14 overlaps the power-receiving coil 23 in plan view. The in vivo-implantable medical device 90 includes a magnetic sheet 13 that contacts a main surface of the coil substrate 12. The magnetic sheet 13 is disposed between the power-receiving coil 23 and the circuit substrate 14.

According to the Third Embodiment, the magnetic sheet 13 helps to prevent the external magnetic flux $\varphi$ from reaching the circuit substrate 14. Therefore, the circuit substrate 14 is not affected by the external magnetic flux $\varphi$ despite being disposed so as to overlap the power-receiving coil 23 in plan view.

Fourth Embodiment

In a Fourth Embodiment, an in vivo-implantable medical device is described that receives power from a power-transmitting coil that is outside of its housing by forming an electromagnetic resonance field between the power-receiving coil of the in vivo-implantable medical device and the power-transmitting coil.

Figure 9:
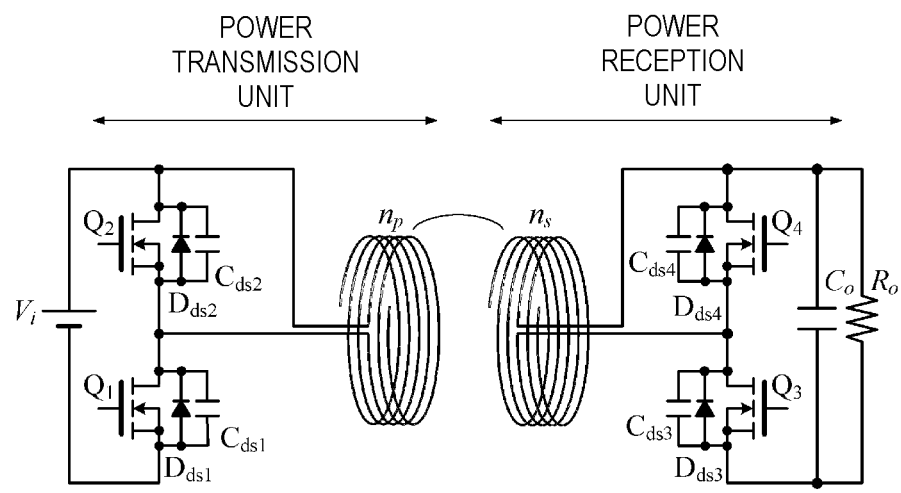
FIG. 9 is a circuit diagram of a power supply system of an in vivo-implantable medical device according to a Fourth Embodiment, the power supply system consisting of a power transmission unit of a power-transmitting device and a power reception unit of an in vivo-implantable medical device.
Figure 10:
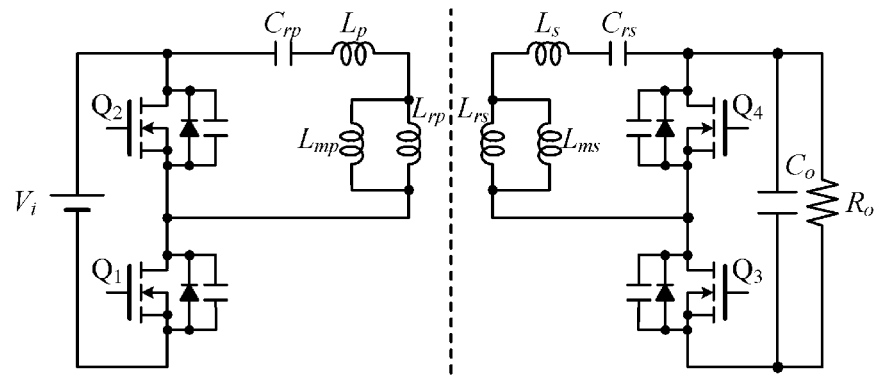
FIG. 10 is an equivalent circuit diagram of the power supply system illustrated in FIG. 9.

FIG. 9 is a circuit diagram of a power supply system of an in vivo-implantable medical device according to the Fourth Embodiment, the power supply system consisting of a power transmission unit of a power-transmitting device and a power reception unit of the in vivo-implantable medical device. FIG. 10 is an equivalent circuit diagram of the power supply system illustrated in FIG. 9.

An input section of the power transmission unit is supplied with an input power supply Vi. The power transmission unit includes a power-transmitting coil np and an AC current generating circuit that is electrically connected to the power-transmitting coil np. The power reception unit includes a power-receiving coil ns and a power reception circuit that is electrically connected to the power-receiving coil ns.

The power-transmitting coil np and the power-receiving coil ns are helical coils and center portions thereof serve as input/output portions. Therefore, the power-transmitting coil np has equivalent inductances Lp, Lmp, and Lrp and an equivalent capacitance Crp, which together form a power transmission resonant circuit. Similarly, the power-receiving coil ns has equivalent inductances Ls, Lms, and Lrs and an equivalent capacitance Crs, which together form a power reception resonant circuit. The winding axes of these two helical coils are substantially aligned with each other (substantially coaxial), and this results in the electric field energy and magnetic field energy interacting with each other to form an electromagnetic resonance field between the power-transmitting coil np and the power-receiving coil ns.

The above-described AC current generating circuit includes a first switch circuit consisting of an equivalent parallel connection circuit made up of a switching element Q1, a diode Dds1, and a capacitor Cds1 and a second switch circuit consisting of an equivalent parallel connection circuit made up of a switching element Q2, a diode Dds2, and a capacitor Cds2.

Switching of the switching elements Q1 and Q2 is controlled by a switching control circuit, which is not illustrated. An AC voltage and an AC current are supplied to the power-transmitting coil np by switching the switching element Q1 and the switching element Q2 on and off in an alternating manner.

The switching control circuit switches the switching element Q1 and the switching element Q2 at a prescribed operation frequency so as to intermittently apply a DC voltage the power transmission resonant circuit and generate a resonant current. This results in the voltage between the two ends of the first switch circuit and the second switch circuit having a sinusoidal waveform having a half wave every half period. For example, the switching operation is performed at 6.78 MHz or 13.56 MHz, which are international industrial, scientific and medical (ISM) bands.

The power reception circuit includes a third switch circuit consisting of a parallel connection circuit equivalently made up of a switching element Q3, a diode Dds3, and a capacitor Cds3, a fourth switch circuit consisting of a parallel connection circuit equivalently made up of a switching element Q4, a diode Dds4, and a capacitor Cds4, and a smoothing capacitor Co. The third switch circuit and the fourth switch circuit form a power reception rectification circuit that rectifies a resonant current generated by the power-receiving coil ns.

The switching elements Q3 and Q4 are controlled by a switching control circuit, which is not illustrated, and rectification is performed in synchronization with changes in direction of the resonant current flowing in the power-receiving coil ns in order to supply a DC current to a load Ro.

In the Fourth Embodiment, the power reception resonant circuit is provided and a resonant current is caused to flow in the power-receiving coil ns, and as a result, a large power-reception power is obtained due to magnetic flux density being increased in a magnetic path where magnetic flux interlinks with the power-receiving coil ns while avoiding the body part 31 (refer to FIG. 4) and eddy current loss due to eddy currents generated by the external magnetic flux φ interlinking with the body part 31 is reduced.

Finally, the descriptions of the above embodiments are illustrative in all points and are not restrictive. A person skilled in the art can make modifications and changes as appropriate. The scope of the present disclosure is defined by the following claims rather than by the above-described embodiments. In addition, changes from the embodiments that are within the scope of equivalents to the scope of the claims are included in the scope of the present disclosure.

What is claimed is:

1. An in vivo-implantable medical device comprising:
    a housing that includes a body part having an opening and a protruding part configured to close the opening, the housing configuring a sealed inner space, the body part including a metallic biocompatible material and the protruding part including a non-metallic biocompatible material;
    a power-receiving coil that is disposed in a part of the inner space configured by the protruding part and that receives power by interlinking with external magnetic flux generated by an AC current flowing in an externally located power-transmitting coil; and
    a circuit substrate having a power reception circuit electrically connected to the power-receiving coil and that is disposed in the inner space further from a protruding end of the protruding part than the power-receiving coil,
    wherein
    the protruding part is structured so that, for a magnetic path along which the external magnetic flux passes, a magnetic path in which the magnetic flux interlinks with the power-receiving coil while avoiding the body part is created, and the protruding part is configured to reduce eddy current loss caused by eddy currents generated by the external magnetic flux interlinking with the body part.

2. The in vivo-implantable medical device according to claim 1, further comprising:
    a power reception resonant circuit,
    wherein a resonant current is caused to flow in the power-receiving coil and, as a result, a power-reception power having a magnitude is obtained due to magnetic flux density being increased in the magnetic path where magnetic flux interlinks with the power-receiving coil while avoiding the body part, and eddy current loss due to eddy currents generated by the external magnetic flux interlinking with the body part is reduced.

3. The in vivo-implantable medical device according to claim 1, further comprising:
    a magnetic sheet disposed between the power-receiving coil and the circuit substrate, wherein a magnetic path is created in which magnetic flux interlinks with the power-receiving coil while avoiding the body part.

4. The in vivo-implantable medical device according to claim 3, wherein
    the magnetic sheet is disposed in a part of the inner space configured by the protruding part and creates a magnetic path in which magnetic flux interlinks with the power-receiving coil while avoiding the body part.

5. The in vivo-implantable medical device according to claim 1, wherein
    the non-metallic biocompatible material is sapphire, ruby, glass, or a ceramic.

6. The in vivo-implantable medical device according to claim 1, wherein the metallic biocompatible material is a material containing titanium or a titanium alloy.

7. The in vivo-implantable medical device according to claim 1, wherein
a dimension of the body part in a protruding direction of the protruding part is larger than a length by which the protruding part protrudes, and is smaller than a dimension of the body part in an arbitrary direction perpendicular to the protruding direction of the protruding part.

8. The in vivo-implantable medical device according to claim 2, further comprising:
a magnetic sheet disposed between the power-receiving coil and the circuit substrate, wherein a magnetic path is created in which magnetic flux interlinks with the power-receiving coil while avoiding the body part.

9. The in vivo-implantable medical device according to claim 2, wherein
the non-metallic biocompatible material is sapphire, ruby, glass, or a ceramic.

10. The in vivo-implantable medical device according to claim 3, wherein
the non-metallic biocompatible material is sapphire, ruby, glass, or a ceramic.

11. The in vivo-implantable medical device according to claim 4, wherein
the non-metallic biocompatible material is sapphire, ruby, glass, or a ceramic.

12. The in vivo-implantable medical device according to claim 2, wherein
the metallic biocompatible material is a material containing titanium or a titanium alloy.

13. The in vivo-implantable medical device according to claim 3, wherein
the metallic biocompatible material is a material containing titanium or a titanium alloy.

14. The in vivo-implantable medical device according to claim 4, wherein
the metallic biocompatible material is a material containing titanium or a titanium alloy.

15. The in vivo-implantable medical device according to claim 5, wherein
the metallic biocompatible material is a material containing titanium or a titanium alloy.

16. The in vivo-implantable medical device according to claim 2, wherein
a dimension of the body part in a protruding direction of the protruding part is larger than a length by which the protruding part protrudes, and is smaller than a dimension of the body part in an arbitrary direction perpendicular to the protruding direction of the protruding part.

17. The in vivo-implantable medical device according to claim 3, wherein
a dimension of the body part in a protruding direction of the protruding part is larger than a length by which the protruding part protrudes, and is smaller than a dimension of the body part in an arbitrary direction perpendicular to the protruding direction of the protruding part.

18. The in vivo-implantable medical device according to claim 4, wherein
a dimension of the body part in a protruding direction of the protruding part is larger than a length by which the protruding part protrudes, and is smaller than a dimension of the body part in an arbitrary direction perpendicular to the protruding direction of the protruding part.

19. The in vivo-implantable medical device according to claim 5, wherein
a dimension of the body part in a protruding direction of the protruding part is larger than a length by which the protruding part protrudes, and is smaller than a dimension of the body part in an arbitrary direction perpendicular to the protruding direction of the protruding part.

20. The in vivo-implantable medical device according to claim 6, wherein
a dimension of the body part in a protruding direction of the protruding part is larger than a length by which the protruding part protrudes, and is smaller than a dimension of the body part in an arbitrary direction perpendicular to the protruding direction of the protruding part.

* * * * *